(12) United States Patent
Jenkins

(10) Patent No.: US 7,530,983 B1
(45) Date of Patent: May 12, 2009

(54) SURGICAL DEVICE FOR REMOVING POLYPS

(76) Inventor: Alma F. Jenkins, 2002 Harris St., Goldsboro, NC (US) 27530

( * ) Notice: Subject to any disclaimer, the term of this patent is extended or adjusted under 35 U.S.C. 154(b) by 928 days.

(21) Appl. No.: 10/667,674

(22) Filed: Sep. 22, 2003

(51) Int. Cl.
*A61B 17/24* (2006.01)
(52) U.S. Cl. ...................................... 606/110
(58) Field of Classification Search ................ 606/113, 606/114, 127, 37, 39, 46, 110, 41–52
See application file for complete search history.

(56) References Cited

U.S. PATENT DOCUMENTS

| 5,035,688 | A | 7/1991 | Inui |
| 5,122,147 | A | 6/1992 | Sewell, Jr. |
| 5,336,227 | A | 8/1994 | Nakao et al. |
| 5,417,697 | A | 5/1995 | Wilk et al. |
| 5,423,830 | A | 6/1995 | Schneebaum et al. |
| 5,462,553 | A | * 10/1995 | Dolgin .................. 606/113 |
| 5,486,182 | A | 1/1996 | Nakao et al. |
| 5,906,620 | A | * 5/1999 | Nakao et al. ............ 606/113 |
| 5,989,264 | A | 11/1999 | Wright |
| 6,783,525 | B2 | * 8/2004 | Greep et al. ............. 606/41 |
| 2002/0165555 | A1 | * 11/2002 | Stein et al. ............. 606/113 |

* cited by examiner

*Primary Examiner*—Kevin T Truong
(74) *Attorney, Agent, or Firm*—Coats & Bennett, P.L.L.C.

(57) ABSTRACT

A method and apparatus for removing polyps from an inner lining of an internal cavity uses a polyp-severing head extending from one end of a sheath. The polyp-severing head comprises a conductive hook or conductive forceps for engaging the polyp and for discharging electrical energy into the engaged polyp to sever the polyp from the inner lining of the internal cavity. In exemplary applications, a physician manipulates the polyp-severing head around the polyp and engages the polyp near the inner lining surface. The physician then discharges electrical energy into the polyp via the polyp-severing head. The electrical energy transferred from the polyp-severing head to the engaged portion of the polyp severs the polyp from the inner lining surface.

16 Claims, 7 Drawing Sheets

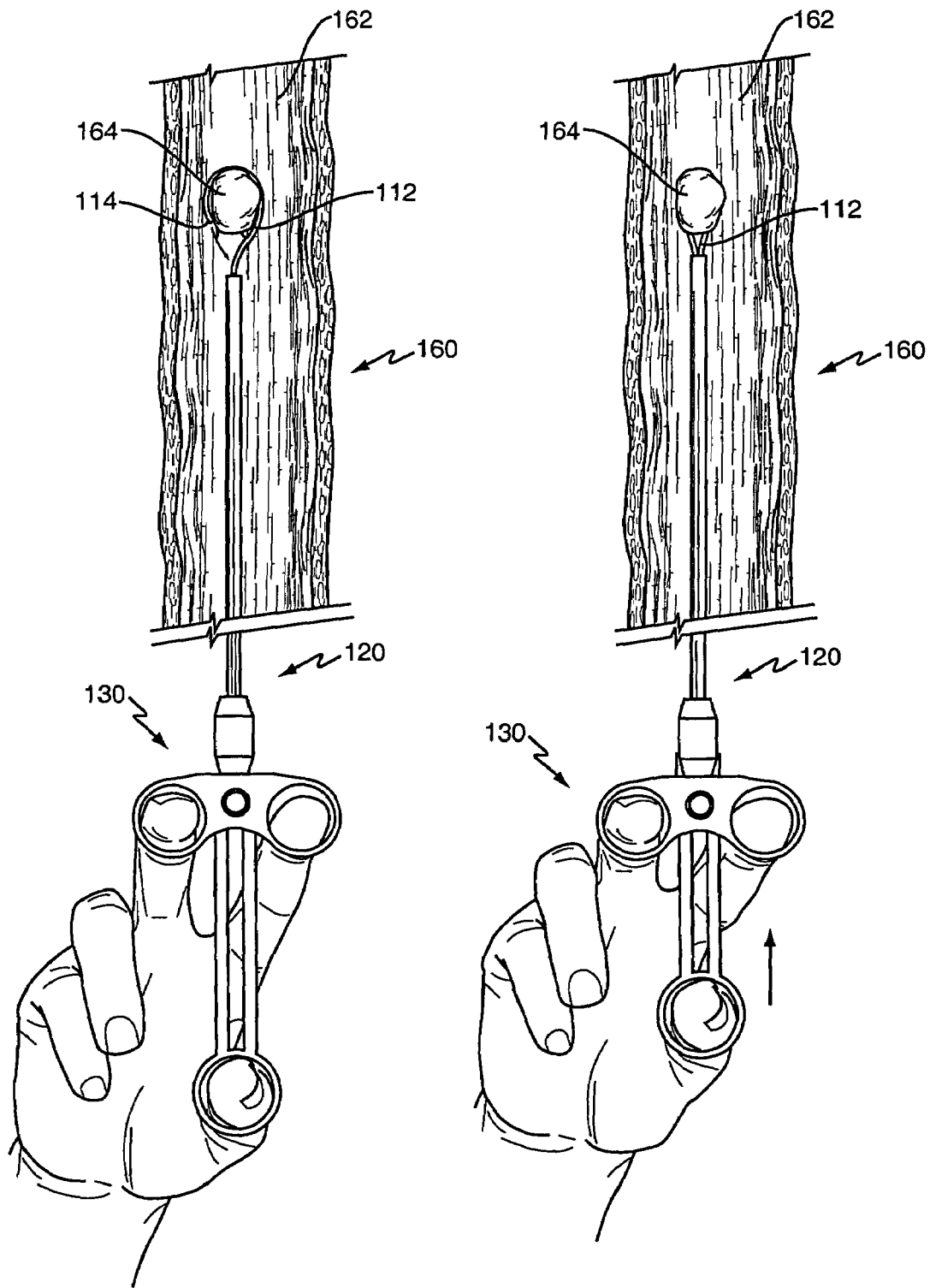
*FIG. 6A*  *FIG. 6B*

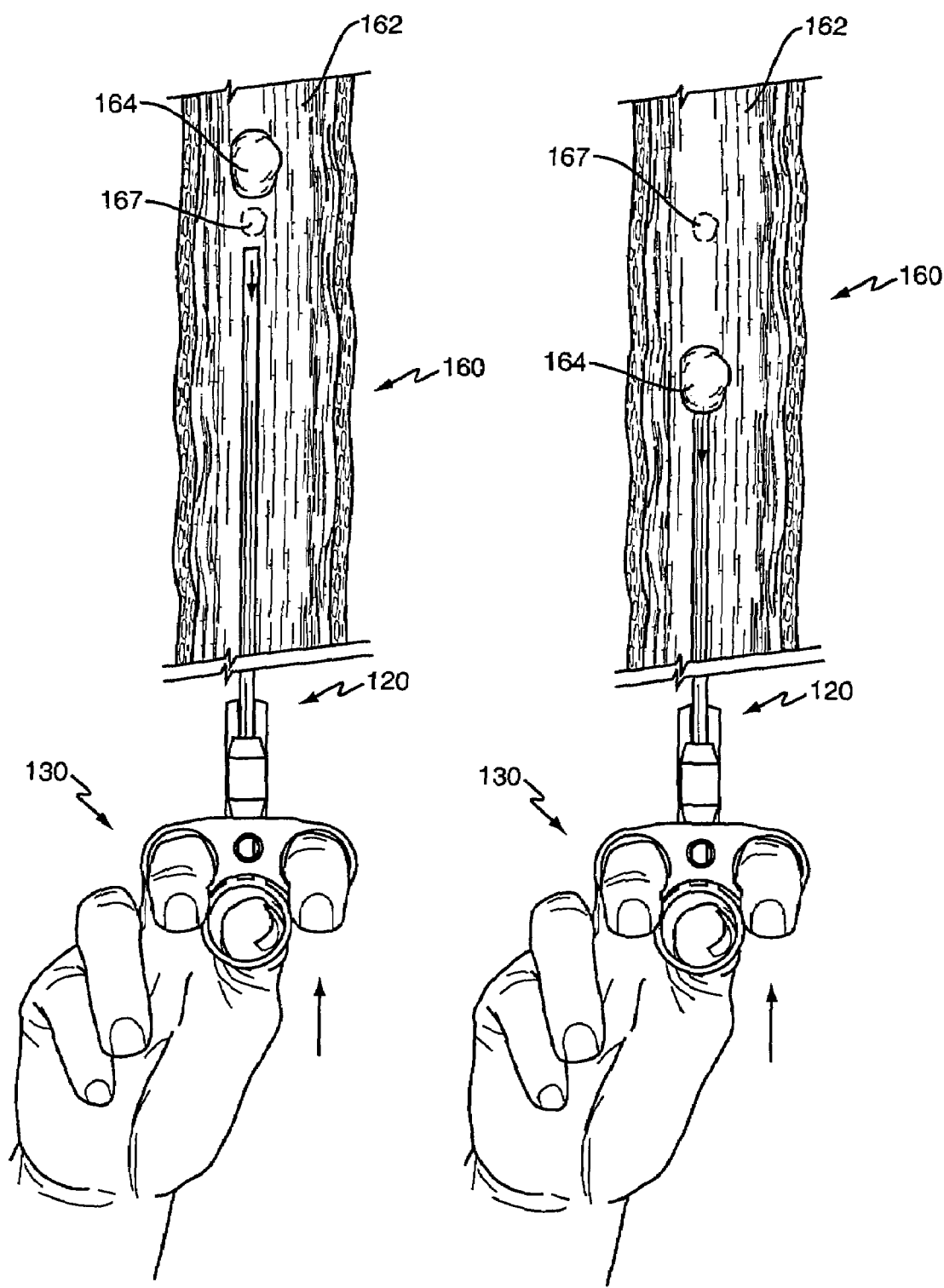
FIG. 6C  FIG. 6D

SURGICAL DEVICE FOR REMOVING POLYPS

BACKGROUND OF THE INVENTION

The present invention generally relates to a method and apparatus for removing polyps from the inner lining of an internal cavity, and more particularly to a method and apparatus for engaging and removing polyps from the large intestine or colon.

Polyps are fleshy growths that form on an inner lining of an internal cavity, such as the stomach, uterus, urinary tract, esophagus, colon, etc. Colon polyps are the most common and the most dangerous. This is largely due to the fact that approximately 75% of all colon polyps are cancerous polyps, also known as adenomas. Further, as colon polyps grow larger, the chance of colon cancer increases. Because colon cancer is the second leading cause of cancer related death in the United States, most medical professionals recommend the removal of any colon polyp.

As late as the mid 1960's, removing colon polyps required entering the colon by cutting through the abdomen wall. Such major surgery had numerous possible complications and a long recovery time. Colonoscopic polypectomy, an endoscopic procedure for examining and removing polyps from the colon, was introduced in the late 1960's. This procedure uses endoscopic technology to capture and remove polyps from the colon or large intestine. Typically a physician inserts an endoscopic snare, such as a sharp edged or conductive loop, into the colon, and fits the loop over the head of the polyp. The physician then cuts or burns through the base of the polyp with the loop. The physician may capture the severed polyp using suction, baskets, nets, etc. While the prior techniques have proven effective, conventional snares cannot always fit over relatively large polyps, making it difficult, if not impossible, to use conventional endoscopic procedures to remove such relatively large polyps.

SUMMARY OF THE INVENTION

The present invention is directed to a method and apparatus for removing polyps from an inner lining of an internal cavity. In an exemplary embodiment, the apparatus includes a polyp-severing head extending from one end of a sheath. The polyp-severing head includes a conductive hook for engaging the polyp. The conductive hook discharges electrical energy into an engaged polyp to sever the polyp from the inner lining of the internal cavity.

In exemplary applications, a physician manipulates the conductive hook around the polyp and engages the polyp. The physician then discharges electrical energy into the polyp via the conductive hook. The electrical energy transferred from the conductive hook to the engaged portion of the polyp severs the polyp from the inner lining surface.

In another exemplary embodiment, the polyp-severing head includes forceps for engaging the polyp. The forceps include conductive opposing inner edges that discharge electrical energy into the engaged polyp to sever the polyp from the inner lining of the cavity. In this embodiment, the physician opens the forceps near the polyp, manipulates the open forceps around to polyp, and closes the forceps to engage the polyp. The physician then discharges electrical energy into the forceps to sever the polyp from the inner lining surface.

BRIEF DESCRIPTION OF THE DRAWINGS

FIG. 6A illustrates the polyp severing head of the polyp surgical device disposed around a polyp.

FIG. 6B shows the polyp severing head of FIG. 6A withdrawn/retracted around the polyp.

FIG. 6C illustrates the severed polyp and the collapsed polyp-severing head.

FIG. 6D illustrates the polyp surgical device removing the severed polyp from the internal cavity of the patient.

DETAILED DESCRIPTION OF THE INVENTION

Figure 1:
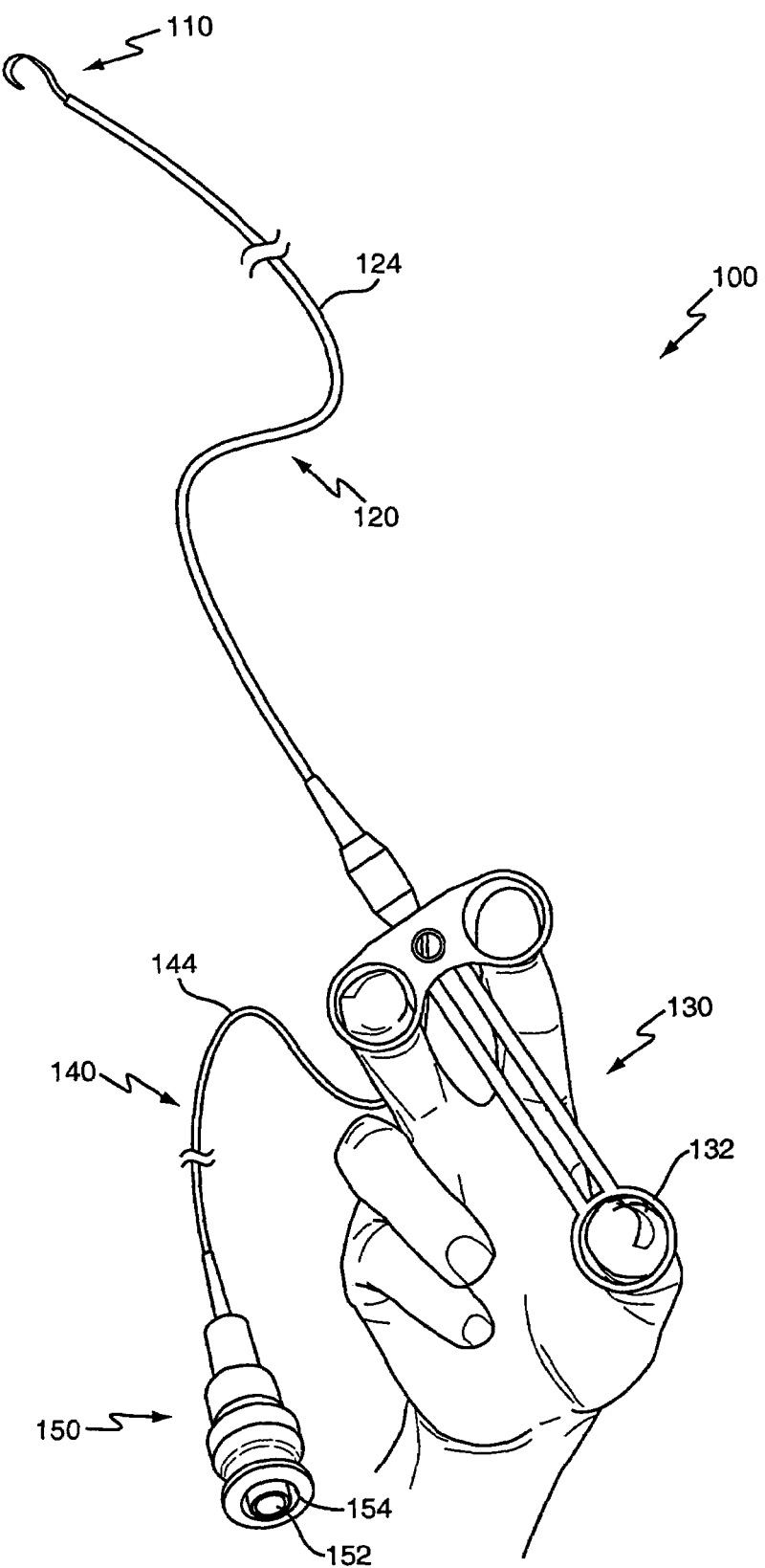
FIG. 1 is a perspective view of the polyp surgical device of the present invention.

FIG. 1 illustrates a polyp surgical device 100 for removing polyps from an internal cavity according to the present invention. Polyp surgical device 100 comprises polyp-severing head 110, lead cable 120, handle 130, connector cable 140, and connector 150. A lead wire 122 disposed in an outer sheath 124 of lead cable 120 (see FIG. 5) mechanically connects polyp-severing head 110 to handle 130. Manipulating handle 130 causes relative movement between polyp-severing head 110 and outer sheath 124 of lead cable 120, as described further below. In addition, lead wire 122 electrically connects polyp-severing head to a connector wire 142 disposed in an outer sheath 144 of connector cable 140 (see FIG. 5) at handle 130. Connector wire 142 also electrically connects to connector 150, as described further below. As a result, connector wire 142 and lead wire 122 electrically connect polyp-severing head 110 to connector 150.

Figure 2:
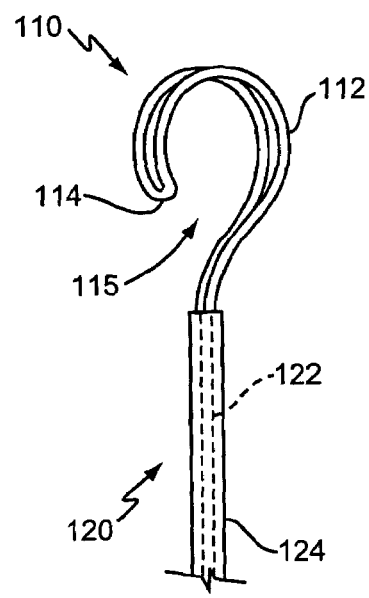
FIG. 2 illustrates the polyp severing head of the polyp surgical device of FIG. 1.

FIG. 2 illustrates an embodiment for polyp-severing head 110 according to the present invention. Polyp-severing head 110 comprises a continuation of lead wire 122 extending outwardly from outer sheath 124 and shaped generally as a hook 112. At a tip 114 of hook 112, the wire loops around, follows the general contour of hook 112, and re-enters outer sheath 124. The hook 112 illustrated in FIG. 2 provides a complete electrical path from connector 150 to hook 112 as described further below. In addition, hook 112 provides an open space 115 between tip 114 and the body of the hook 112. It should be appreciated that the general shape of the hook 112 could vary, and that the manner of directing electrical energy through the hook 112 may also vary. Therefore, the present invention is not limited to the conductive hook 112 described above.

To ensure that conductive wire 122 does not short out inside outer sheath 124 of lead cable 120, lead cable 120 may include an insulator (not shown) for isolating the wires 122 encased in outer sheath 124. Alternately, the wires 122 disposed in outer sheath 124 may be encased in an insulative sleeve (not shown). Conductive hook 112 may also include an insulative backing, such as a flexible plastic backing (not shown), to prevent electrical shorts along hook 112.

Figure 3A:
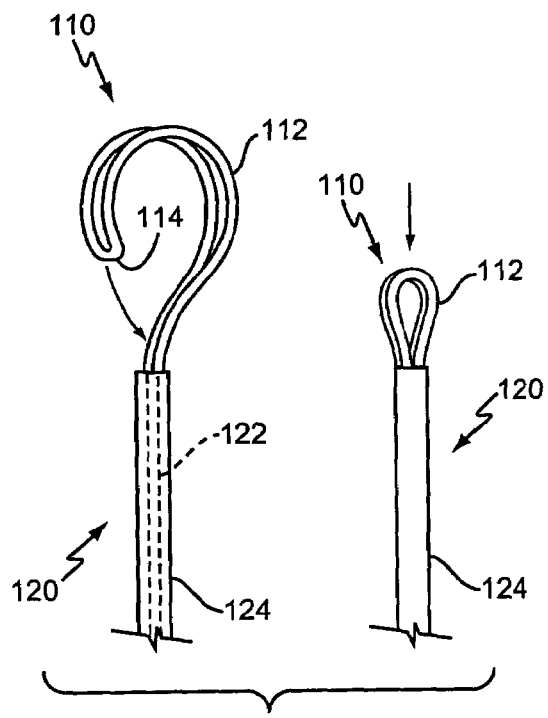
FIG. 3A illustrates the polyp-severing head of FIG. 2 withdrawing into a collapsed configuration.
Figure 3B:
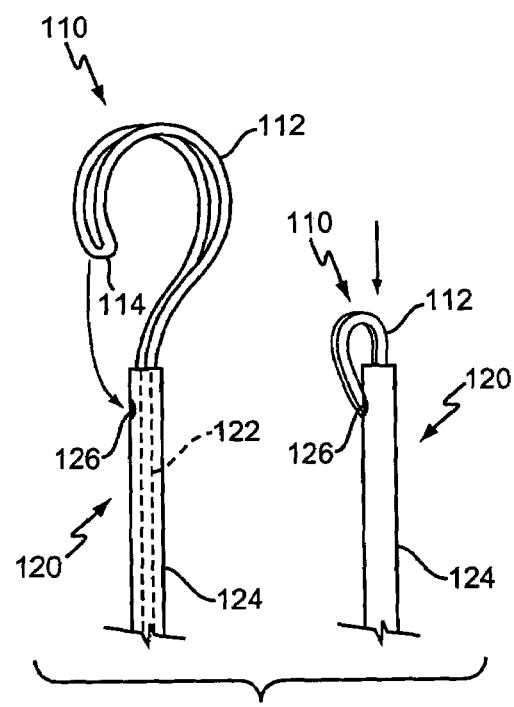
FIG. 3B illustrates the polyp-severing head of FIG. 2 withdrawing into an alternate collapsed configuration.

In a preferred embodiment, conductive hook 112 is capable of moving with respect to the outer sheath 124. In such embodiments, moving control 132 on handle 130 back and forth extends and withdraws conductive hook 112 with respect to outer sheath 124. In a first embodiment, moving control 132 withdraws conductive hook 112 partially or wholly into outer sheath 124, as shown in FIG. 3A. Alternatively, moving control 132 withdraws conductive hook 112 into outer sheath 124 until an external opening 126 in lead cable 120 secures tip 114 of conductive hook 112, as shown in FIG. 3B. It will be appreciated by those skilled in the art that the relative movement of conductive hook 112 is not limited to the embodiments described above.

Figure 4:
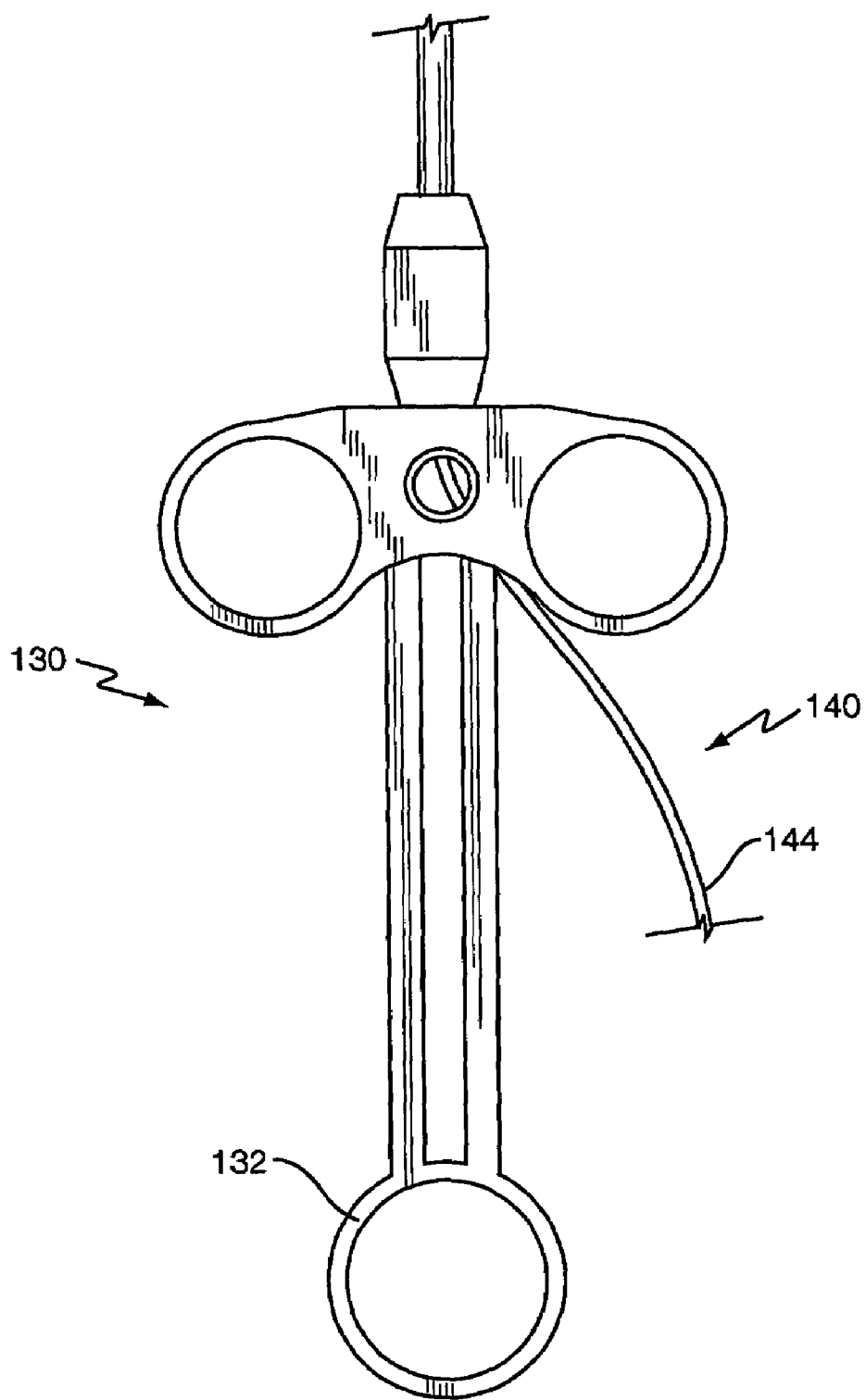
FIG. 4 illustrates the handle of the polyp surgical device of FIG. 1.

FIG. 4 illustrates an exemplary handle 130 applicable to the present invention. While the present invention utilizes the handle 130 shown in FIG. 4, those skilled in the art will recognize that other known handles are equally applicable to the present invention. Handle 130 provides a movable control, such as a thumb control 132, for mechanically controlling conductive hook 112. In one embodiment, thumb control 132 is operatively connected to conductive hook 112 via conductive wire 122. As thumb control 132 is moved back and forth, conductive hook 112 extends and retracts from and into outer sheath 124.

Figure 5:
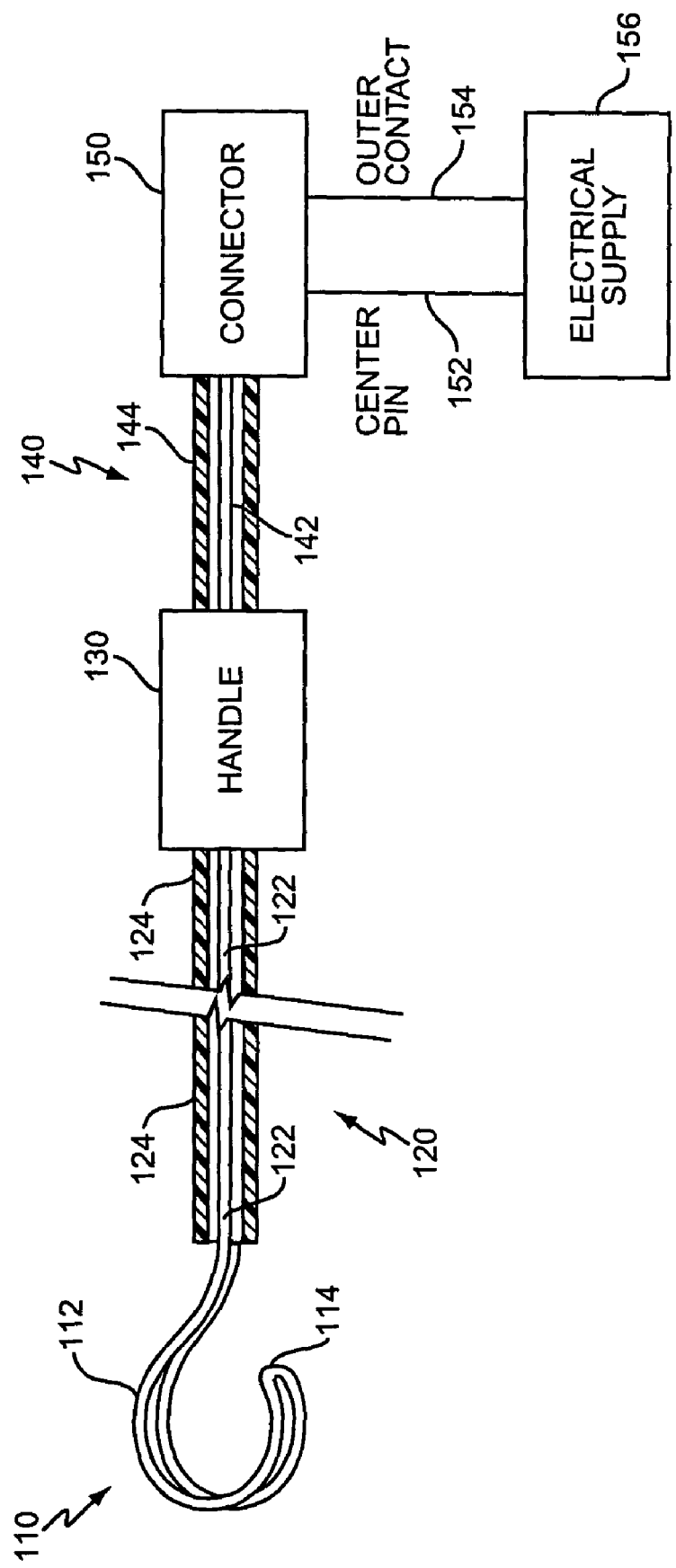
FIG. 5 is a schematic view showing the connector and controls for the polyp surgical device.

As shown in FIG. 4, one end of connector cable 140 extends from handle 130. Attaching a connector 150 disposed on the opposite end of connector cable 140 to an electrical supply 156 electrically connects conductive hook 112 to electrical supply 156, as shown in FIG. 5. Details regarding electrical supply 156 are not addressed in the present application because such electrical supplies are well known in the art and are commercially available. Connector 150 may be any connector known in the art that includes at least two pins. In a preferred embodiment, connector 150 comprises a 2-contact coaxial connector (see FIG. 1) with an outer ground contact 154 connected to one end of connector wire 142 and a center power pin 152 connected to another end of connector wire 142. Activation of a properly connected electrical supply 156 causes polyp-severing head 110 to discharge electrical energy.

FIGS. 6A-6D illustrate a surgical procedure that uses the polyp surgical device 100 of FIGS. 1-5 to remove a polyp 164 attached to surface 162 of an internal cavity, such as a colon 160. While the following describes the removal of colon polyps, those skilled in the art will appreciate that the present invention may remove polyps from any internal cavity, such as the stomach, uterus, urinary tract, esophagus, or the like.

A physician inserts polyp surgical device 100 into colon 160, via an external opening of a patient, until conductive hook 112 is proximate a polyp 164. The physician may use a wide variety of techniques to locate polyp 164. Such techniques are well known in the art, and therefore, are not discussed further herein. Once appropriately positioned, the physician manipulates conductive hook 112 around polyp 164 such that polyp 164 passes through the opening 115, as illustrated in FIG. 6A. The physician then engages polyp 164 (FIG. 6B) by manipulating control 132 of handle 130 to withdraw conductive hook 112 about polyp 164 to engage polyp 164. The physician then activates electrical supply 156 while continuing to withdraw conductive hook 112 about polyp 164 to simultaneously strangle and sever polyp 164 from surface 162 while cauterizing the resulting wound 167 (FIG. 6C).

Once severed from surface 162, the physician may remove severed polyp 164 from the colon by various conventional means. For example, the physician may capture the severed polyp 164 with the conductive hook 112 and pull the severed polyp 164 from the colon by withdrawing the polyp surgical device 100 from the colon. Alternatively, the outer sheath 124 may be operatively connected to a vacuum source (not shown). The lead cable 120 may then be utilized to create a vacuum in the outer sheath 124. After completely withdrawing conductive hook 112 into lead cable 120 (FIG. 6C), the physician may secure the severed polyp 164 to the tip of lead cable 120 by activating the vacuum source to apply suction to the severed polyp 164. While severed polyp 164 is secured to the tip of lead cable 120, the physician removes the polyp surgical device 100 and the severed polyp 165 from colon 160 (FIG. 6D).

Figure 7A:
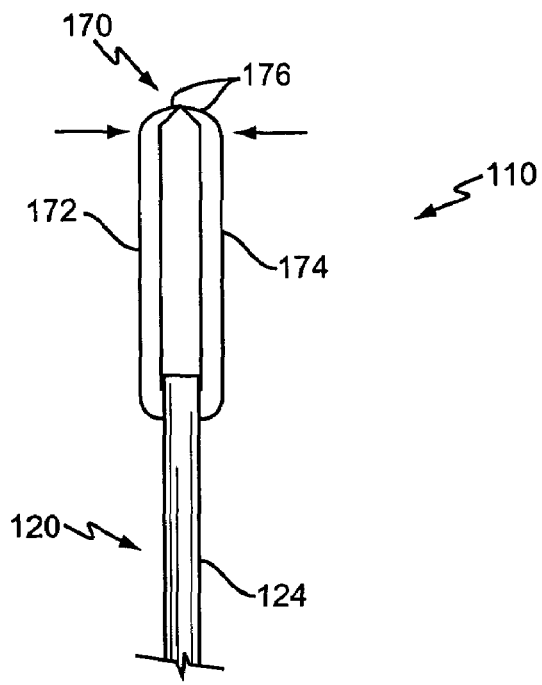
FIG. 7A illustrates another exemplary polyp-severing head in a closed position.
Figure 7B:
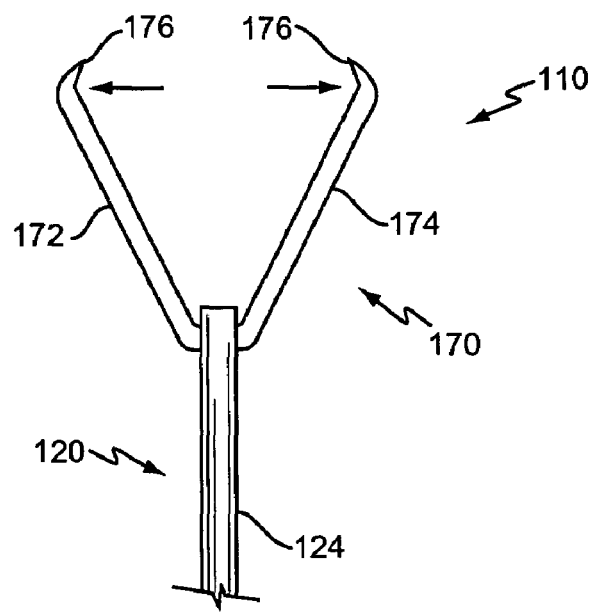
FIG. 7B illustrates the polyp-severing head of FIG. 7A in an open position.

The polyp surgical device 100 of the present invention is not limited to the conductive hook 112 described above. For example, as illustrated in FIGS. 7A and 7B, polyp-severing head 110 of the present invention may comprise a pair of conductive forceps 170. Conductive forceps 170 comprise a left prong 172 and a right prong 174 connected at one end of lead cable 120. For example, a pivot pin, a hinge, a spring-loaded joint, etc., may connect prongs 172, 174 at the tip of lead cable 120. Conductive forceps 170 may be opened or closed by manipulating control 132 of handle 130.

Left prong 172 and right prong 174 electrically connect to connector 150 via lead cable 120 and handle 130 according to any means know in the art. For example, in a first embodiment, a power wire (not shown) may connect left prong 172 to center pin 152 of connector 150, while a ground wire (not shown) may connect right prong 174 to outer contact 154 of connector 150. As a result, conductive forceps 170 will only dissipate electrical energy when the tips 176 of prongs 172, 174 complete the electrical circuit. Alternatively, in a second embodiment, each prong 172, 174 of conductive forceps 170 may comprise one or more embedded wires (not shown) that provide a complete electrical circuit from each prong 172, 174 to connector 150. As a result, each prong 172, 174 of the conductive forceps 170 of the second embodiment may dissipate electrical energy even when the tips 176 do not come into contact.

In an exemplary procedure, a physician inserts the conductive forceps 170 of FIG. 7A into the colon of a patient while conductive forceps 170 are in a closed position (FIG. 7A). Once appropriately positioned proximate polyp 164, the physician opens conductive forceps 170 and positions polyp 164 between the separated prongs 172, 174. The physician then engages polyp 164 by manipulating control 132 of handle 130 to grasp polyp 164 between the prongs 172, 174 of conductive forceps 170. Once the conductive forceps 170 have engaged polyp 164, the physician activates electrical supply 156 while closing the conductive forceps 170 to simultaneously strangle and sever polyp 164 from surface 162 and to cauterize the resulting wound 167. Once severed, the physician may remove polyp 164 from the colon by any means well known in the art.

In summary, the above described methods and apparatus may easily engage and remove polyps, even larger polyps that do not fit within conventional snare techniques. Therefore, the polyp-removing methods and devices of the present invention are applicable to a larger percentage of polyps than conventional techniques, providing a physician with additional less-invasive treatment options for relatively large polyps.

The foregoing description and drawings describe and illustrate the present invention in detail. However, the foregoing only describes some embodiments of a polyp-severing device. Accordingly, the present invention may be carried out in specific ways other than those set forth herein without departing from the essential characteristics of the invention. The present embodiments are, therefore, to be considered in all respects as illustrative and not restrictive, and all changes coming within the meaning and equivalency range of the appended claims are intended to be embraced therein.

What is claimed is:

1. A method of removing a polyp from a surface comprising:
   manipulating a conductive hook around the polyp;
   engaging the polyp with said conductive hook; and
   severing the polyp from said surface by discharging electrical energy from said conductive hook into the polyp.

2. The method of claim 1 including maintaining the conductive hook in a generally constant hook shape while manipulating the hook, engaging the polyp with the hook, and severing the poly from the surface.

3. The method of claim 2 wherein engaging the polyp comprises retracting said conductive hook about the polyp until said conductive hook engages a stem of the polyp.

4. The method of claim 3 wherein retracting said conductive hook about the polyp comprises retracting at least a portion of said conductive hook into a sheath.

5. The method of claim 2 wherein severing the polyp includes cauterizing the polyp and the surface.

6. The method of claim 2 further comprising retracting at least a portion of said conductive hook into a sheath after severing the polyp from the surface.

7. The method of claim 6 wherein retracting at least a portion of said conductive hook into said sheath comprises encasing said conductive hook with said sheath.

8. The method of claim 6 wherein retracting at least a portion of said conductive hook into said sheath comprises inserting a tip of said conductive hook into an opening in said sheath.

9. The method of claim 6 wherein the polyp is removed from an inner lining of an internal cavity.

10. The method of claim 9 wherein removing the severed polyp from the internal cavity comprises applying suction to the severed polyp.

11. The method of claim 2 including removing the polyp from a colon.

12. The method of claim 2 wherein said hook is movable relative to a terminal end of a sheath, and wherein the procedure for removing the polyp includes extending said hook from the terminal end of said sheath such that an open space exists between a terminal end of said hook and the terminal end of said sheath; and passing the polyp through the opening between the terminal end of said hook and the terminal end of said sheath.

13. The method of claim 12 wherein after the polyp has been passed between the opening between the terminal end of said hook and the terminal end of said sheath, moving said hook towards the terminal end of said sheath and engaging the polyp with said hook as said hook moves towards the terminal end of said sheath.

14. The method of claim 12 further comprising retracting said hook with respect to said sheath such that the terminal end of said hook is inserted into an opening formed in said sheath.

15. The method of claim 1 including inserting the conductive hook into the colon of a patient wherein there is at least one polyp in the colon; and contacting the polyp with the conductive hook and conducting electrical energy into the polyp and simultaneously strangling and severing the polyp with the conductive hook.

16. The method of claim 15 including retracting at least a portion of the conductive hook within a sheath during the method of removing the polyp.

* * * * *